United States Patent [19]
Kusuzawa

[11] Patent Number: 5,748,298
[45] Date of Patent: May 5, 1998

[54] LIGHT RECEIVING OPTICAL SYSTEM HAVING A LIGHT SELECTOR INTEGRAL WITH A LENS AND PARTICLE ANALYZER INCLUDING THE SAME

[75] Inventor: Hideo Kusuzawa, Kobe, Japan

[73] Assignee: Toa Medical Electronics Co., Ltd., Hyogo, Japan

[21] Appl. No.: 713,650

[22] Filed: Sep. 13, 1996

[30] Foreign Application Priority Data

Sep. 14, 1995 [JP] Japan .................. 7-236798
Sep. 14, 1995 [JP] Japan .................. 7-236799

[51] Int. Cl.⁶ .................................. G01N 21/00
[52] U.S. Cl. ............................. 356/73; 356/343
[58] Field of Search ................... 356/337, 338, 356/339, 343, 73, 414, 416, 419; 359/738, 739

[56] References Cited

U.S. PATENT DOCUMENTS 4,566,792  1/1986  Suzuki ........................ 356/319
4,989,960  2/1991  Thomas ....................... 359/738
5,140,462  8/1992  Kyogoku et al. ............. 359/588
5,155,543  10/1992  Hirako ........................ 356/343
5,276,552  1/1994  Kohmoto et al. ............ 359/738

FOREIGN PATENT DOCUMENTS 60-262041  12/1985  Japan .
61-35333   2/1986   Japan .

*Primary Examiner*—Frank G. Font
*Assistant Examiner*—Amanda Merlino

[57] ABSTRACT

A light receiving optical system and a particle analyzer including the same which can be miniaturized and simplified are provided. The light receiving optical system includes a light receiving lens provided integrally with a light selector for selecting and outputting light by attenuating part of the light incident on the light receiving lens.

12 Claims, 8 Drawing Sheets

VERTICAL AXIS 1V/DIV  HORIZONTAL AXIS 2μsec/DIV

VERTICAL AXIS 1V/DIV  HORIZONTAL AXIS 2μsec/DIV

LIGHT RECEIVING OPTICAL SYSTEM HAVING A LIGHT SELECTOR INTEGRAL WITH A LENS AND PARTICLE ANALYZER INCLUDING THE SAME

BACKGROUND OF THE INVENTION

1. Field of the Invention

The present invention relates to a light receiving optical system and a particle analyzer comprising the same and more particularly to a light receiving optical system comprising a light receiving lens for receiving intended light and used in various optical apparatuses and a particle analyzer, comprising the light receiving optical system, for measuring the size, shape, property or the like of particles within a sample containing particulate components such as blood corpuscles and various cells by sheathing the sample with a sheath solution in a flow cell and by irradiating a sheathed sample flow formed in the flow cell to measure scattered light and fluorescent light emitted from the sheathed sample flow.

2. Description of Related Art

Hitherto, a flow cytometer has been known widely as an apparatus for analyzing particles. FIG. 7 shows a detecting section of a typical prior art flow cytometer.

In the figure, a sheathed sample flow containing particulate components such as blood corpuscles and various cells is formed in a flow cell 104 by sheathing the sample together with a sheath solution as an outer layer thereof (the particulate components and the fluid flow in a direction vertical to the page). An irradiating optical system 101 comprises an argon laser beam source 102 and a condenser lens unit 103. Light output from the irradiating optical system 101 is directed to a sheathed sample flow 113 formed in the front flow cell 104.

A front light receiving optical system 105 for receiving light emitted in the front direction from the sheathed sample flow 113 in the flow cell 104 comprises a beam stopper 106, an objective lens unit 107 and a photodiode 108. The beam stopper 106 blocks front direct light which is output from the argon laser beam source 102 and transmits through the flow cell 104 in the front direction. The objective lens unit 107 detects scattered light and fluorescent light (front scattered light and front fluorescent light) emitted in the front direction from the sheathed sample flow 113 in the flow cell 104. The photodiode 108 detects the front fluorescent light which has passed through the objective lens unit 107.

A side light receiving optical system 109 for receiving light emitted in the side direction from the sheathed sample flow 113 in the flow cell 104 comprises an objective lens unit 110, a sharp-cut filter 111 as a wavelength selection filter and a photo-multiplier 112. The objective lens unit 110 detects scattered light and fluorescent light (side scattered light and side fluorescent light) emitted in the side direction from the sheathed sample flow 113 in the flow cell 104. The photo-multiplier 112 detects the side fluorescent light which has passed through the objective lens unit 110 and the filter 111.

In such flow cytometer, beside the objective lens unit 107 which takes a relatively large volumetric portion of the front light receiving optical system, the beam stopper 106 and a mechanism (not shown) for adjusting it are disposed between the flow cell and the objective lens unit 107, thus considerably increasing the volume taken by the front light receiving optical system.

Further, beside the objective lens unit 110 which takes a relatively large volumetric portion of the side light receiving optical system, the sharp cut filter 111 is disposed between the objective lens unit 110 and the photo-multiplier 112, thus considerably increasing the volume taken by the side light receiving optical system.

This kind of problem has existed not only in particle analyzers such as the flow cytometer, but also in a light receiving optical system of various optical apparatuses.

Accordingly, in view of such problem, it is a primary object of the present invention to provide a light receiving optical system and a particle analyzer comprising the same which can be miniaturized and simplified.

SUMMARY OF THE INVENTION

According to one aspect of the present invention, there is provided a light receiving optical system includes a light receiving lens on which a light selector means for selecting and outputting light by attenuating part of the light incident to the light receiving lens is integrally provided.

This kind of light receiving optical system is applicable to optical apparatuses in general. The light receiving lens receives intended light such as light emitted from a light source and light emitted from a spot irradiated by the light source.

Because the inventive light receiving optical system comprises a light receiving lens which is provided integrally with a light selector means for selecting and outputting light by attenuating part of the light incident to the light receiving lens, no beam stopper nor its micro-adjustment mechanism needs to be provided separately. Accordingly, it allows intended light to be received preferentially by blocking unnecessary incident light and also the optical system to be simplified and miniaturized. It is noted that the entrance surface of the light receiving lens may be flat or curved.

DETAILED DESCRIPTION OF THE PREFERRED EMBODIMENTS

Figure 1:
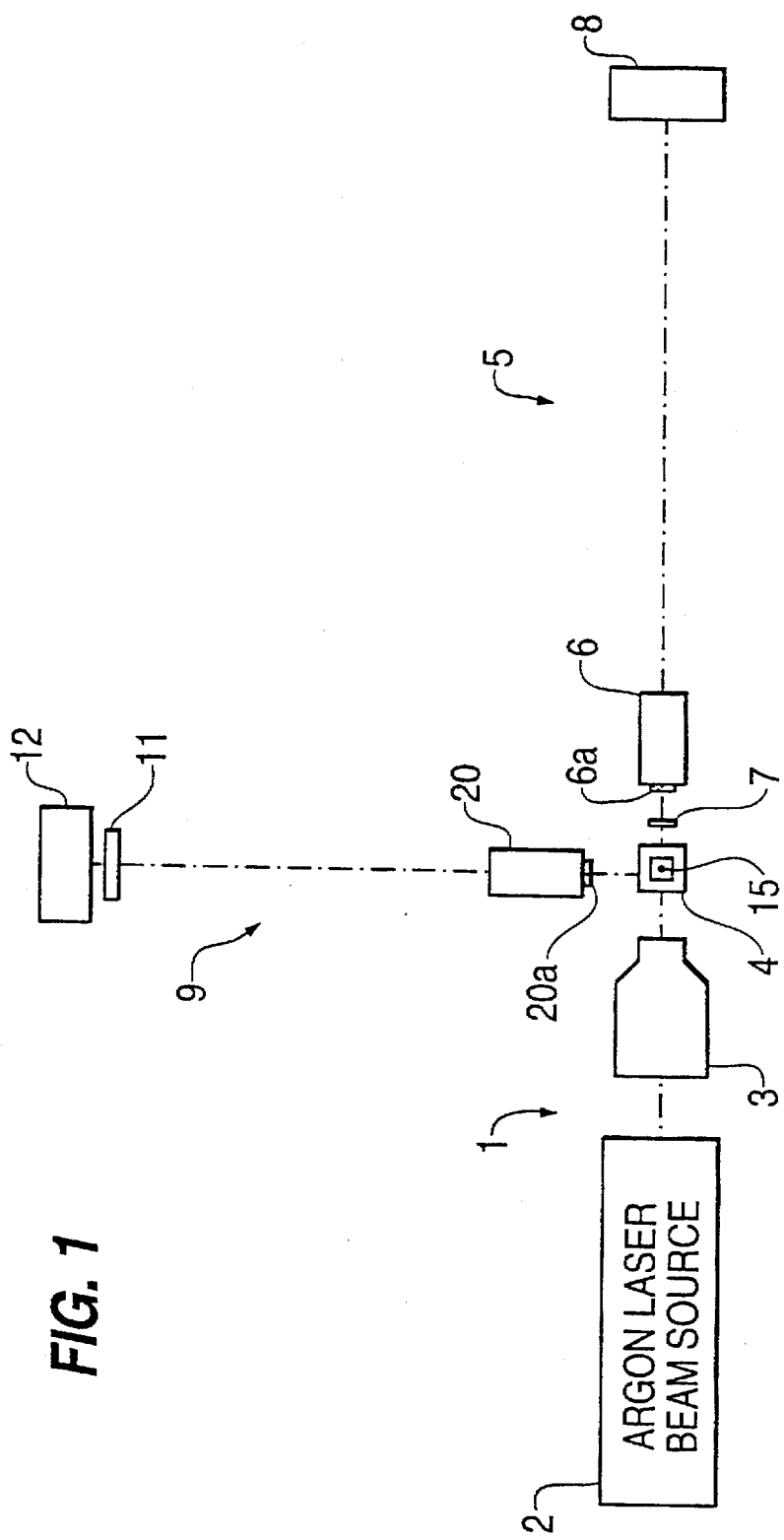
FIG. 1 is a schematic explanatory drawing showing a structure of a detecting section of a flow cytometer according to a first embodiment of the present invention.

Preferably, a beam stopper or a wavelength selection filter for example is used for the light selecting means.

The beam stopper on the entrance surface of the light receiving lens is formed by using a high precision masking technology in IC fabrication processes. That is, it is formed by evaporating an IC masking material such as Cr, Au-Cr, Au or the like on the entrance surface. It allows the beam stopper to be provided in high precision and readily.

The shape of the beam stopper may be arbitrarily set corresponding to its purpose, such as in a one-dimensional shape or in a two-dimensional shape (circular, elliptical and various polygons). Because the shape of the beam stopper may be set arbitrarily, only unnecessary light may be blocked effectively (front direct light from the irradiating optical system when this light receiving optical system is used for the particle analyzer) while transmitting necessary light (light from particles when this light receiving optical system is used for the particle analyzer) as much as possible. It allows light signals to be detected with a good S/N ratio.

It is preferable to create a groove in part of the entrance surface of the light receiving lens and to mask so as to cover the groove portion in forming the beam stopper. Thereby, a double structure by which light is reflected both by the surface of the groove and by the surface of the mask may be realized. Because incident light is reflected by the surface of the groove and by the surface of the mask, a more suitable beam stopper may be formed in view of its purpose of blocking unnecessary light.

That is, the wavelength selection filter may be a filtering film formed on the light receiving lens. This filtering film is specifically an interference film formed by a dielectric substance such as $SiO_2$, $MgO_2$, $MgF_2$ or the like.

The wavelength selection filter may be composed of a filtering member optically bonded to the light receiving lens. For example, they are integrated by optically bonding one end surface of the light receiving lens with one end surface of a colored glass which is the filtering member.

Further, the wavelength selection filter may be made of a filtering member which also functions as the light receiving lens. For example, the light receiving lens may be fabricated from a colored glass which is the filtering member.

The light receiving lens may be a conventional objective lens or a rod lens. When a rod lens is used for the light receiving lens, the optical system may be miniaturized and simplified further as compared to the case of an objective lens because the size of the lens can be small in general.

A rod lens is a lens whose shape is cylindrical and whose refractive index is distributed so as to change parabolically and continuously from a center axis of the cylindrical lens to a peripheral surface thereof. It is called also as an index distributed lens, a distributed index lens or a SELFOC lens. When such rod lens is employed, light incident to one end surface of the rod lens propagates through the cylinder while describing a sine curve or helical optical path and is output from the other end surface.

A lens 1 to 2 mm in diameter and 3 to 30 mm in length is used for the rod lens.

According to another aspect of the present invention, there is provided a particle analyzer comprising the light receiving optical system comprising a light receiving lens provided integrally with light selecting means for selecting and outputting light by attenuating part of the light incident to the light receiving lens. This particle analyzer is used as a flow cytometer having a flow cell for example.

A known flow cell for forming a sheathed sample flow containing particulate components such as blood corpuscles and various cells may be used for the flow cell. By using such flow cell, the sheathed sample flow is formed by sheathing the sample with a sheath solution as an outer layer. The sheathed sample flow is irradiated by an irradiating optical system comprising an argon laser beam source and a condenser lens unit for example.

The light receiving optical system receives light emitted from the sheathed sample flow in the flow cell irradiated by the irradiating optical system to detect desired scattered light and fluorescent light. This light receiving optical system is disposed at a predetermined place corresponding to the purpose of detection. That is, when it is to be used as a front light receiving optical system for receiving light emitted in the front direction from the sheathed sample flow in the flow cell, it is disposed in front of the sheathed sample flow in the flow cell, when it is to be used as a side light receiving optical system for receiving light emitted in the side direction from the sheathed sample flow, it is disposed on the side of the sheathed sample flow in the flow cell and when it is to be used as the front and side light receiving optical systems, it is disposed in front of and on the side of the sheathed sample flow in the flow cell.

The light receiving optical system includes the front light receiving optical system having the light receiving lens for receiving the light emitted in the front direction from the sheathed sample flow in the flow cell and the side light receiving optical system for receiving the light emitted in the side direction from the sheathed sample flow.

A light receiving optical system used for the front light receiving optical system may be one in which (1) the beam stopper for blocking unnecessary input light is provided on the entrance surface of the light receiving lens; (2) the beam stopper is provided by masking part of the entrance surface of the light receiving lens; (3) the beam stopper is provided in a one-dimensional shape on part of the entrance surface of the light receiving lens; (4) the beam stopper is provided in a two-dimensional shape on part of the entrance surface of the light receiving lens; (5) the beam stopper is provided by creating a groove on part of the entrance surface of the lens and by masking the groove; and (6) the light receiving lens is a rod lens having the beam stopper in any one of (1) through (5) above.

Further, a light receiving optical system used for the side light receiving optical system may be one in which (1) the light receiving lens which is provided integrally with the wavelength selection filter is provided; (2) the wavelength selection filter is a filtering film formed on the light receiving lens; (3) the wavelength selection filter is made of a filtering member optically boned to the light receiving lens; (4) the wavelength selection filter is made of a filtering member which also functions as the light receiving lens; and (5) the light receiving lens is a rod lens having the wavelength selection filter in any one of (1) through (4) above.

The optical systems may be miniaturized and simplified in the particle analyzer comprising such light receiving optical systems.

The above and other advantages of the invention will become more apparent in the following description and the accompanying drawings.

[Concrete Embodiments of the Invention]

Four embodiments of the present invention will be explained in detail below with reference to the drawings. It is noted that the present invention is not confined only to these embodiments.

[First Embodiment]

FIG. 1 shows a detecting section of the flow cytometer as a particle analyzer according to a first embodiment of the present invention.

In the figure, an irradiating optical system 1 comprises an argon laser beam source 2 and a condenser lens unit 3. Light output from the irradiating optical system 1 is directed to a front flow cell 4. A sheathed sample flow 15 is formed in the flow cell 4 by sheathing a sample containing particulate components such as blood corpuscles and various cells with a sheath solution as an outer layer thereof (the particulate components and the fluid flow in a direction vertical to the page).

A front light receiving optical system 5 for receiving light emitted in the front direction from the sheathed sample flow 15 in the flow cell 4 comprises a beam stopper 7, a rod lens unit 6 and a photodiode 8. The beam stopper 7 blocks front direct light which is output from the argon laser beam source 2 and transmits through the flow cell 4 in the front direction. The rod lens unit 6 detects scattered light and fluorescent light (front scattered light and front fluorescent light) emitted in the front direction from the sheathed sample flow 15 in the flow cell 4. The photodiode 8 detects the front fluorescent light which has passed through the rod lens unit 6.

A side light receiving optical system 9 for receiving light emitted in the side direction from the sheathed sample flow 15 in the flow cell 4 comprises a rod lens unit 20 in which a wavelength selection filter is incorporated and a photo-multiplier 12. The rod lens unit 20 detects scattered light and fluorescent light (side scattered light and side fluorescent light) emitted in the side direction from the sheathed sample flow 15 in the flow cell 4. The photo-multiplier 12 detects the side fluorescent light which has passed through the rod lens unit 20.

Figure 2:
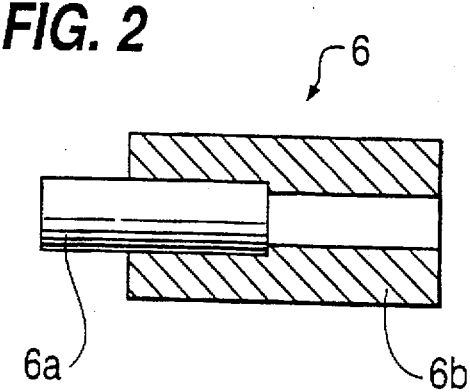
FIG. 2 is an explanatory drawing showing an enlarged structure of a rod lens unit in a front light receiving optical system of the detecting section of the flow cytometer in FIG. 1.

FIG. 2 is an enlarged view of the rod lens unit 6 comprising a rod lens 6a as the light receiving lens and a cylindrical member 6b to which part of the rod lens 6a is inserted and is held by bonding with glass soldering.

The rod lens 6a is formed of a member fabricated by grinding the SML (SELFOC Micro Lens) H18 manufactured by Nippon Sheet Glass Co., Ltd. and has a cylindrical shape with 1.8 mm in diameter and 10.0 mm in length whose one end surface (closer to the flow cell), i.e. an entrance surface, is flat.

Figure 7:
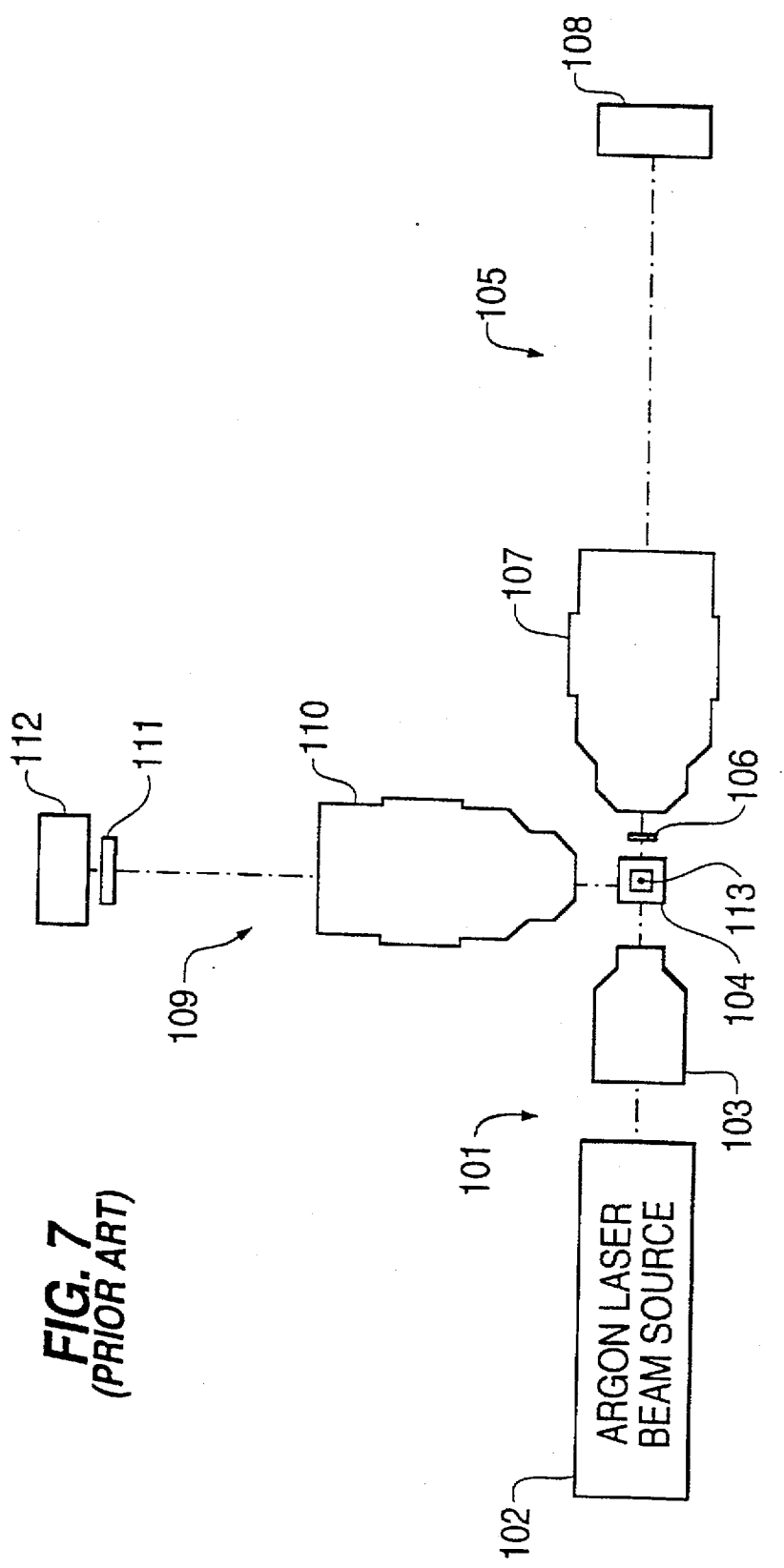
FIG. 7 is a schematic explanatory drawing showing a structure of a detecting section of a prior art flow cytometer.

Although the lens unit 110 and the filter 111 have been used separately in the detecting section of the prior art flow cytometer as shown in FIG. 7, they are constructed integrally in the detecting section of the flow cytometer of the first embodiment to miniaturize and simplify it. That is, they are integrated so as to be able to handle the lens and filter as one part by forming a filtering member on the surface of the lens, by bonding the lens and the filtering member or by composing the lens itself by the filtering member.

Figure 3:
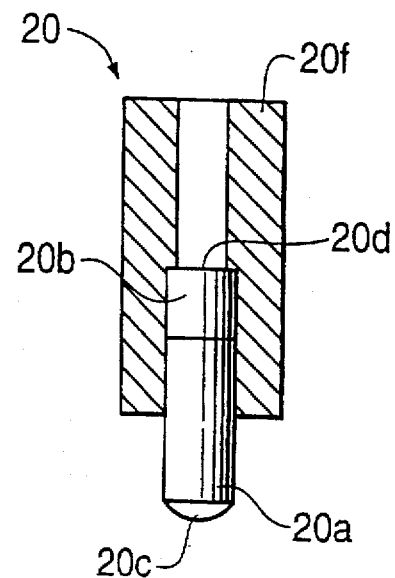
FIG. 3 is an explanatory drawing showing an enlarged structure of a rod lens unit in a side light receiving optical system in the detecting section of the flow cytometer in FIG. 1.

That is, as shown in FIG. 3, the rod lens 20 is composed of a cylindrical rod lens 20a formed of the member described above fabricated by grinding the H18, a cylindrical colored glass 20b as a wavelength selection filter and a cylindrical member 20f into which part of them are inserted and held by bonding with glass soldering. An output surface of the rod lens 20a is optically bonded to one end surface of the colored glass 20b. Further, the filtering member is formed on an entrance surface of the rod lens 20a to form an interference film 20c as a wavelength selection filter. An AR coating 20d is formed on an exit surface of the colored glass 20b.

Figure 8:
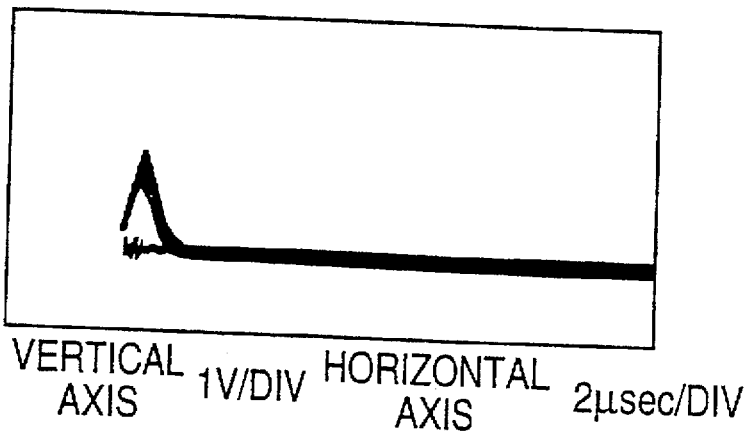
FIG. 8 is an explanatory graph showing an output of side fluorescent light when it is detected by an objective lens unit used in the detecting section of the prior art flow cytometer.
Figure 9:
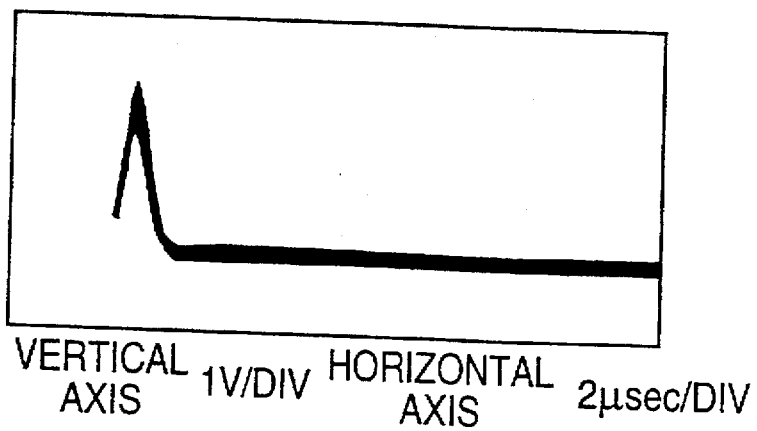
FIG. 9 is an explanatory graph showing an output of side fluorescent light when it is detected by the rod lens used in the detecting section of the flow cytometer of the first embodiment of the present invention.

FIGS. 8 and 9 show waveforms of side scattered light signals detected when latex particles 7 μm in diameter to which fluorescent dye is attached are supplied into the flow cell as particles to be studied respectively in the prior art flow cytometer equipped with the objective lens unit 110 and the flow cytometer of the first embodiment of the present invention equipped with the rod lens unit 20. As it is apparent by comparing them, a signal which is about twice of that of the prior art (FIG. 8) is detected in the first embodiment (FIG. 9). This happens because of a difference of substantial light condensing abilities of the lenses. Generally, the objective lens is composed of many lenses and as the number of lenses increases, reflection on the surface of the lenses accumulate, thus dropping its transmission efficiency. The rod lens 20a which will do just by one lens is effective also in this point.

Figure 10:
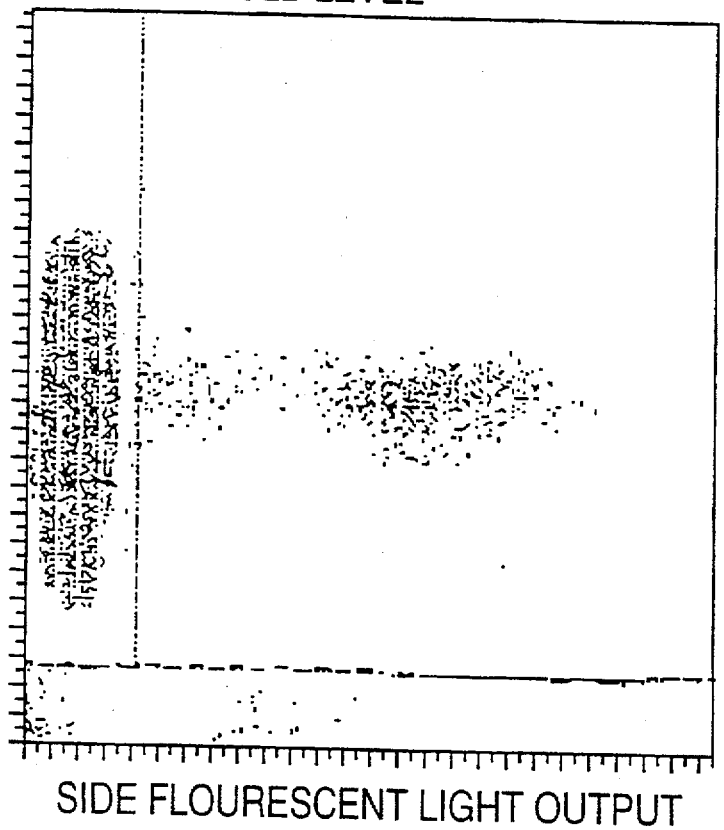
FIG. 10 is an explanatory graph showing a scattergram of the rod lens used in the detecting section of the flow cytometer of the first embodiment of the present invention.

FIG. 10 shows a scattergram taken by arranging the apparatus to measure reticulocyte adjusting particles (RETCHECK®, manufactured by Toa Medical Electronics Co., Ltd.). When the prior art apparatus and the inventive apparatus of the first embodiment were compared concerning the distribution modes of the scattergrams and RET # (number of reticulocytes) and RET % (ratio of reticulocytes) which are counted results, it was found that there is no problem with the apparatus of the first embodiment and that it is possible to replace the prior art objective lens with the rod lens.

Thus, it is preferable to provide the rod lens 20 with the filtering function by itself. It is noted that the technological concept of providing the filter to the light receiving lens is applicable to lenses other than the rod lens as a matter of course and is applicable not only to the light receiving optical system but also to the irradiating optical system.

[Second Embodiment]

Figure 4:
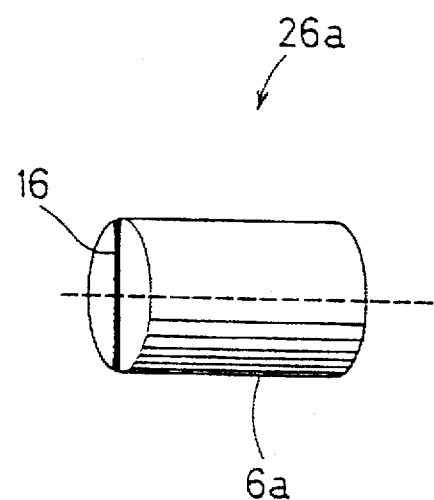
FIG. 4 is an enlarged perspective view showing a rod lens in a front light receiving optical system in the detecting section of the flow cytometer according to a second embodiment of the present invention.

FIG. 4 shows a rod lens 26a for the front light receiving optical system in which a linear beam stopper 16 of 100 to 200 μm in width is formed on the entrance surface of the rod lens 6a so as to cross the center thereof, instead of the rod lens 6a in the first embodiment. The beam stopper 16 blocks front direct light which is output from the argon laser beam source 2 and transmits through the flow cell 4 in the front direction.

The beam stopper 16 is formed by using a high precision masking technique employed in IC fabrication processes. That is, it is formed by evaporating an IC masking material such as Cr, Au-Cr or the like on the entrance surface of the rod lens 6a. Although the beam stopper 16 may be used generally with a light receiving lens other than the rod lens, the rod lens may be said to be advantageous as a lens for forming the beam stopper 16 because a precision of an outside dimension of the light receiving lens has to be good in order to form the beam stopper 16 in high precision.

[Third Embodiment]

Figure 5:
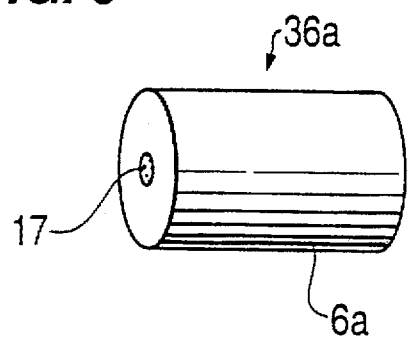
FIG. 5 is an enlarged perspective view showing a rod lens in the front light receiving optical system in the detecting section of the flow cytometer according to a third embodiment of the present invention.

The shape of the beam stopper may be arbitrarily set. Although the beam stopper 16 on the rod lens 26a in FIG. 4 is in a one-dimensional shape having 100 to 200 µm in width, the width may be varied from several tens µm to several hundreds µm depending on its purpose. Further, it is also possible to form it in a two-dimensional shape (circular, elliptical or various polygons) at the center of the entrance surface of the rod lens 6a like a beam stopper 17 on the rod lens 36a shown in FIG. 5. It is noted that the entrance surface of the rod lens 6a may be flat or curved.

[Fourth Embodiment]

Figure 6:
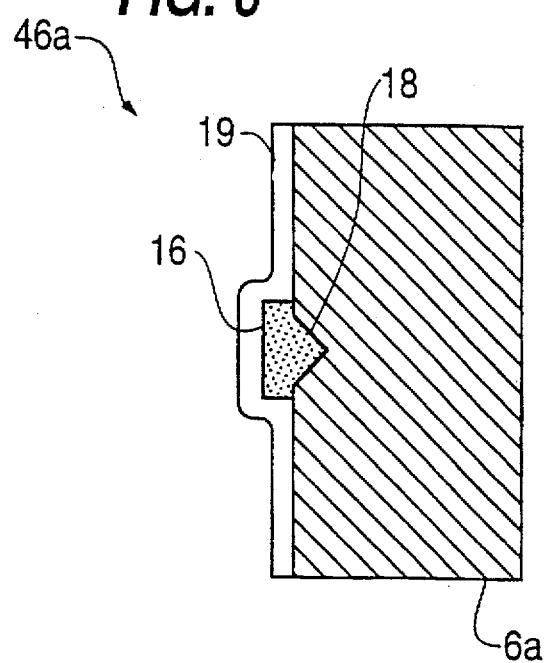
FIG. 6 is an enlarged longitudinal sectional view showing a rod lens in the front light receiving optical system in the detecting section of the flow cytometer according to a fourth embodiment of the present invention.

Preferably, the beam stopper 16 is formed by cutting a part of the entrance surface of the rod lens 6a into a one-dimensional groove 18 having a V-shaped section and to mask so as to cover the groove 18 portion like a rod lens 46a shown in FIG. 6. It is because an double structure may be formed by which light is reflected both by the surface of the groove 18 and the surface of the mask.

A process for fabricating it will be illustrated below. At first, ultrasonic wave is applied to the entrance surface of the rod lens 6a (cylinder 1.8 mm in diameter and 10.0 mm in length whose one end surface, i.e. the entrance surface, is flat) to form the V-shaped groove 18 of 150 µm in width. Then, photoresist is applied to the whole entrance surface. A mask pattern in which a beam stopper of desired shape is patterned is placed on that and is exposed to ultraviolet rays to harden and solidify the photoresist film at the exposed portion. After that, part of the photoresist not exposed to the rays (a part which turns out to be the beam stopper 16) is removed by an organic solvent. Then, Cr is evaporated. Subsequently, the remaining photoresist is removed by chemicals such as sulfuric acid+hydrogen peroxide solution. Finally, an AR coating 19 is the whole surface of the entrance surface.

Figure 11:
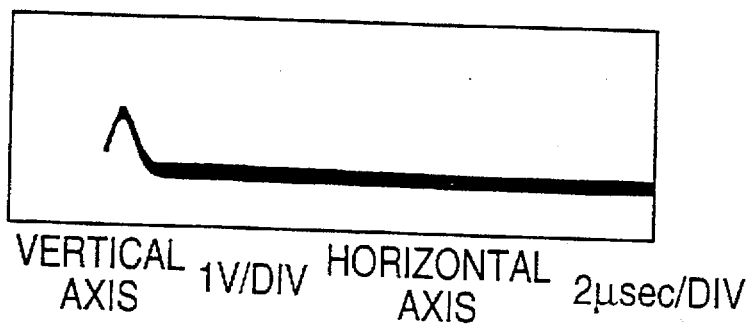
FIG. 11 is an explanatory graph showing an output of front scattered light when it is detected by a beam stopper and the objective lens unit used in the detecting section of the prior art flow cytometer.
Figure 12:
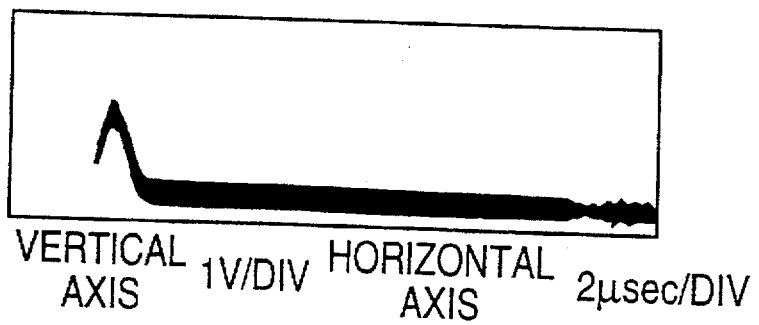
FIG. 12 is an explanatory graph showing an output of front scattered light when it is detected by the rod lens having a beam stopper used in the detecting section of the flow cytometer of the fourth embodiment of the present invention.

FIGS. 11 and 12 show waveforms of measured front scattered light from latex particles of 7 µm in diameter when the prior art flow cytometer shown in FIG. 7 and the flow cytometer of the fourth embodiment in which the rod lens 46a fabricated as described above is used instead of the rod lens 6a in FIG. 1 are used respectively. As it is apparent by comparing them, the one in the fourth embodiment of the present invention is detected as a signal which is about 1.5 times of that of the prior art.

While the preferred embodiments have been described, variations thereto will occur to those skilled in the art within the scope of the present inventive concepts which are delineated by the following claims.

What is claimed is:

1. A light receiving optical system comprising:

a light receiving lens; and a beam stopper, integrally provided on said light receiving lens, for blocking part of the light incident to said light receiving lens at a predetermined portion including a center of an entrance surface of said light receiving lens.

2. The light receiving optical system according to claim 1, wherein said light receiving lens is a rod lens.

3. The light receiving optical system according to claim 1, wherein said beam stopper is provided in a one-dimensional shape on part of an entrance surface of said light receiving lens.

4. The light receiving optical system according to claim 1, wherein said beam stopper is provided in a two-dimensional shape on part of an entrance surface of said light receiving lens.

5. The light receiving optical system according to claim 1, wherein said beam stopper is provided by creating a groove on part of an entrance surface of said light receiving lens and by masking said groove.

6. A light receiving optical system comprising:

a light receiving lens; and a wavelength selection filter, integrally provided on said light receiving lens, for filtering part of light having a predetermined wavelength among the light incident on said light receiving lens.

7. The light receiving optical system according to claim 6, wherein said wavelength selection filter is a filtering film formed on said light receiving lens.

8. The light receiving optical system according to claim 6, wherein said wavelength selection filter is a filtering member optically bonded to said light receiving lens.

9. The light receiving optical system according to claim 6, wherein said wavelength selection filter is formed of a filtering member which functions also as a light receiving lens.

10. A particle analyzer comprising a light receiving optical system including a light receiving lens on which light selecting means for selecting and outputting light by attenuating part of the light incident to said light receiving lens is integrally provided.

11. The particle analyzer according to claim 10, comprising: a flow cell for forming a sheathed sample flow containing particulate components and a front light receiving optical system for receiving light emitted in the front direction from said sheathed sample flow in said flow cell, wherein said light selecting means is a beam stopper, provided on said light receiving lens, for blocking part of the light incident to said light receiving lens at a predetermined spot.

12. The particle analyzer according to claim 10, comprising: a flow cell for having a sheathed sample flow containing particulate components and a side light receiving optical system for receiving light emitted in the side direction from said sheathed sample flow in said flow cell, wherein said light selecting means is a wavelength selection filter, provided on said light receiving lens, for filtering part of light having a predetermined wavelength among the light incident to said light receiving lens.

\* \* \* \* \*